(12) United States Patent
Suzuki

(10) Patent No.: US 12,421,148 B2
(45) Date of Patent: Sep. 23, 2025

(54) METHOD AND SYSTEM FOR STORING BIOMASS RAW MATERIAL

(71) Applicant: TAIYO SERVICE INC., Hamamatsu (JP)

(72) Inventor: Yuji Suzuki, Hamamatsu (JP)

(73) Assignee: TAIYO SERVICE INC., Hamamatsu (JP)

( * ) Notice: Subject to any disclaimer, the term of this patent is extended or adjusted under 35 U.S.C. 154(b) by 721 days.

(21) Appl. No.: 17/619,447

(22) PCT Filed: Nov. 18, 2019

(86) PCT No.: PCT/JP2019/045018
§ 371 (c)(1),
(2) Date: Dec. 15, 2021

(87) PCT Pub. No.: WO2020/255439
PCT Pub. Date: Dec. 24, 2020

(65) Prior Publication Data
US 2022/0402797 A1 Dec. 22, 2022

(30) Foreign Application Priority Data
Jun. 17, 2019 (JP) .................... 2019-111824

(51) Int. Cl.
*C02F 11/04* (2006.01)
*B09B 3/65* (2022.01)

(52) U.S. Cl.
CPC ............... *C02F 11/04* (2013.01); *B09B 3/65* (2022.01); *C02F 2203/006* (2013.01);
(Continued)

(58) Field of Classification Search
CPC ............. C02F 11/04; C02F 2203/006; C02F 2209/001; C02F 2209/02; C02F 2209/06;
(Continued)

(56) References Cited

FOREIGN PATENT DOCUMENTS

| JP | 2003091585 A | * | 3/2003 |
| JP | 2005145774 A | * | 6/2005 |
| JP | 2008284499 A | * | 11/2008 |

OTHER PUBLICATIONS

Google translation of Aoyama (Year: 2003).*
Espacenet translation of Nishioka (Year: 2005).*
Espacenet translation of Ukai (Year: 2008).*

* cited by examiner

*Primary Examiner* — Ekandra S. Miller-Cruz
(74) *Attorney, Agent, or Firm* — FisherBroyles, LLP; Roger L. Browdy; James E. Mrose

(57) ABSTRACT

[Object]To provide a method and a system capable of, when a predetermined amount of biomass raw material is to be stored, controlling fermentation of the biomass raw material and further storing the biomass raw material safely for a predetermined period of time.

[Solving Means]The biomass raw material storage method of the present invention. is configured such that it includes a raw material analysis step of analyzing an amount of nutrients contained in an accepted organic energy resource, a raw material storage tank selection step of selecting, from among a plurality of raw material storage tanks, a raw material storage tank for storing the analyzed organic energy resource as biomass raw material, in reference to a result of the analysis and according to the amounts of nutrients contained in the organic energy resource, and a raw material fermentation controlling step of controlling fermentation of the biomass raw material in the raw material storage tank in which the biomass raw material is stored.

8 Claims, 3 Drawing Sheets

(52) U.S. Cl.
CPC .... *C02F 2209/001* (2013.01); *C02F 2209/02* (2013.01); *C02F 2209/06* (2013.01); *C02F 2209/36* (2013.01)

(58) Field of Classification Search
CPC .. C02F 2209/36; C02F 2209/006; B09B 3/65; C12M 21/04; C12P 5/023; Y02E 50/30
USPC ........................................................ 210/613
See application file for complete search history.

[FIG. 2]

METHOD AND SYSTEM FOR STORING BIOMASS RAW MATERIAL

TECHNICAL FIELD

The present invention relates to a biomass raw material storage method and a biomass raw material storage system for safely storing biomass raw material to be supplied to, for example, a biogas generation apparatus.

BACKGROUND ART

Conventionally, there is known a biogas generation apparatus which generates biogas by anaerobic fermentation from biomass raw material. As the biomass raw material to be supplied to the biogas generation apparatus, for example, organic waste such as food waste or raw garbage is generally used. In a processing system that ferments such organic waste as just described with methane under anaerobic conditions to recover methane gas, the organic waste is suitably pulverized into slurry-like biomass raw material and stored as such into a raw material tank.

For example, it is disclosed that, in the biomass gasification system disclosed in PTL 1, pulverized slurry-like mixture or biomass is supplied to a fermentation tank after being supplied to a raw material tank.

Further, PTL 2 and PTL 3 disclose a method, for a methane fermentation processing system for food waste, of generating and recovering biogas by a methane fermentation process using pulverized slurry-like food waste or food waste mainly consisting of liquid waste, as raw material.

CITATION LIST

Patent Literature

PTL 1

Brochure of PCT Patent Publication No. WO2016/038724

PTL 2

Japanese Patent Laid-open. No. Hei 11-300323

PTL 3

Japanese Patent Laid-open No. 2008-284499

SUMMARY

Technical Problems

However, not only the technologies of the pieces of patent literature mentioned above but also the technology at present cannot be considered as appropriately satisfying marketplace needs, having such a challenge as described below.

In particular, in the biogas generation system described above, food waste crushed into a state of slurry or food waste mainly consisting of liquid waste is used as biomass raw material. Although such kinds of biomass raw material as just mentioned are subsequently used in a methane fermentation step, they are also generally traded in the form of biomass raw material. Further, there has been such an accident that, when such kinds of biomass raw material are stored for a predetermined period of time in a storage tank, control of unintended fermentation sometimes becomes impossible, causing the biomass raw material to overflow from piping of the system and contaminate the surroundings or give off a strong odor.

Therefore, in order to prevent such an accident as described above, there has been a demand for finding out a method of controlling fermentation of biomass raw material and a method of making it possible to store biomass raw material safely for a predetermined period of time.

Taking the challenge described above into consideration, it is an object of the present invention to provide a method capable of, when a predetermined amount of biomass raw material is stored, controlling fermentation of the biomass raw material and storing the biomass raw material safely for a predetermined period of time.

Solution to Problems (1) The biomass raw material storage method of the present invention includes a raw material analysis step of analyzing an amount of nutrients contained in an accepted organic energy resource, a raw material storage tank selection step of selecting, from among a plurality of raw material storage tanks, a raw material storage tank for storing the analyzed organic energy resource as biomass raw material, in reference to a result of the analysis and according to the amounts of nutrients contained in the organic energy resource, and a raw material fermentation controlling step of controlling fermentation of the biomass raw material in the raw material storage tank in which the biomass raw material is stored.

(2) The biomass raw material storage method of the present invention is configured such that, in (1) above, the plurality of raw material storage tanks include at least a carbohydrate-rich tank, a fat-rich tank, a protein-rich tank, a fiber-rich tank, and a mixture type tank, and the tanks are maintained and managed under conditions different from one another.

(3) The biomass raw material storage method of the present invention is configured such that, in (2) above, in the storage tank selection step, the mixture type tank is selected when it is analyzed that a main nutrient does not exist among the nutrients, and for the organic energy resource that contains a nutrient that is the main nutrient, the raw material storage tank classified for the nutrient that is the main nutrient is selected.

(4) The biomass raw material storage method of the present invention is configured such that, in (1) above, in the storage tank selection step, the mixture type tank is a selection destination of the highest priority, and for the organic energy resource that contains a nutrient that is the main nutrient, the raw material storage tank classified for the nutrient that is the main nutrient is selected next.

(5) The biomass raw material storage method of the present invention is configured such that, in any one of (1) to (4) above, a parameter for maintenance and management of a raw material storage tank in the raw material fermentation controlling step includes at least one of a temperature and a pH in the raw material storage tank, and the temperature or the pH is managed in such a manner as to be different among different ones of the raw material storage tanks.

(6) The biomass raw material storage system of the present invention includes resource acceptance means for accepting an organic energy resource, nutrient analysis means for analyzing nutrients of the organic energy resource accepted by the resource acceptance means, main nutrient specification means for specifying a main nutrient that is a main nutrient among the analyzed nutrients, a plurality of raw material storage tanks each for storing the organic energy resource as biomass raw material, raw material storage tank selection means for selecting a storage destination from among the plurality of raw material storage tanks that are different from one another and are classified for the individual nutrients, in reference to the specified main nutrient, and raw material fermentation controlling means for controlling fermentation of the biomass raw material in a storage tank in which biomass raw material is stored.

(7) The biomass raw material storage system of the present invention is configured such that, in (6) above, the resource acceptance means includes a neutralization mixture fluidization tank for fluidizing the organic energy resource that contains liquid or sludge, and crushing means including a crusher for crushing the organic energy resource other than the liquid or the sludge.

(8) The biomass raw material storage system of the present invention is configured such that, in (6) or (7) above, the plurality of raw material storage tanks include at least a carbohydrate-rich tank, a fat-rich tank, a protein-rich tank, a fiber-rich tank, and a mixture type tank.

(9) The biomass raw material storage system of the present invention is configured such that, in (8) above, the raw material storage tank selection means selects the storage destination in reference to selection priority ranking determined advance, and the selection priority ranking is made such that the mixture type tank is a selection destination of the highest priority and a storage destination corresponding to the analyzed main nutrient is selected next.

(10) The biomass raw material storage system of the present invention is configured such that, in any one of (6) to (9) above, it further includes reception means for receiving information regarding biomass raw material used by a client, and supply biomass raw material determination means for determining a storage tank for the biomass raw material to be supplied to the client, in reference to nutrients of the biomass raw material of the client.

Advantageous Effect of Invention

According to the biomass raw material storage method and the biomass raw material storage system of the present invention, when a predetermined amount of biomass raw material is stored, it is possible to control fermentation of the biomass raw material and further store the biomass raw material safely for a predetermined period of time.

Further, according to the biomass raw material storage method and the biomass raw material storage system of the present invention, also when biomass raw material is to be traded, it is possible to control unintended fermentation of the biomass raw material and perform safe transportation.

DESCRIPTION OF EMBODIMENT

In the following, an embodiment for carrying out the present invention is described.

First Embodiment

Biomass Raw Material Storage Method

Figure 1:
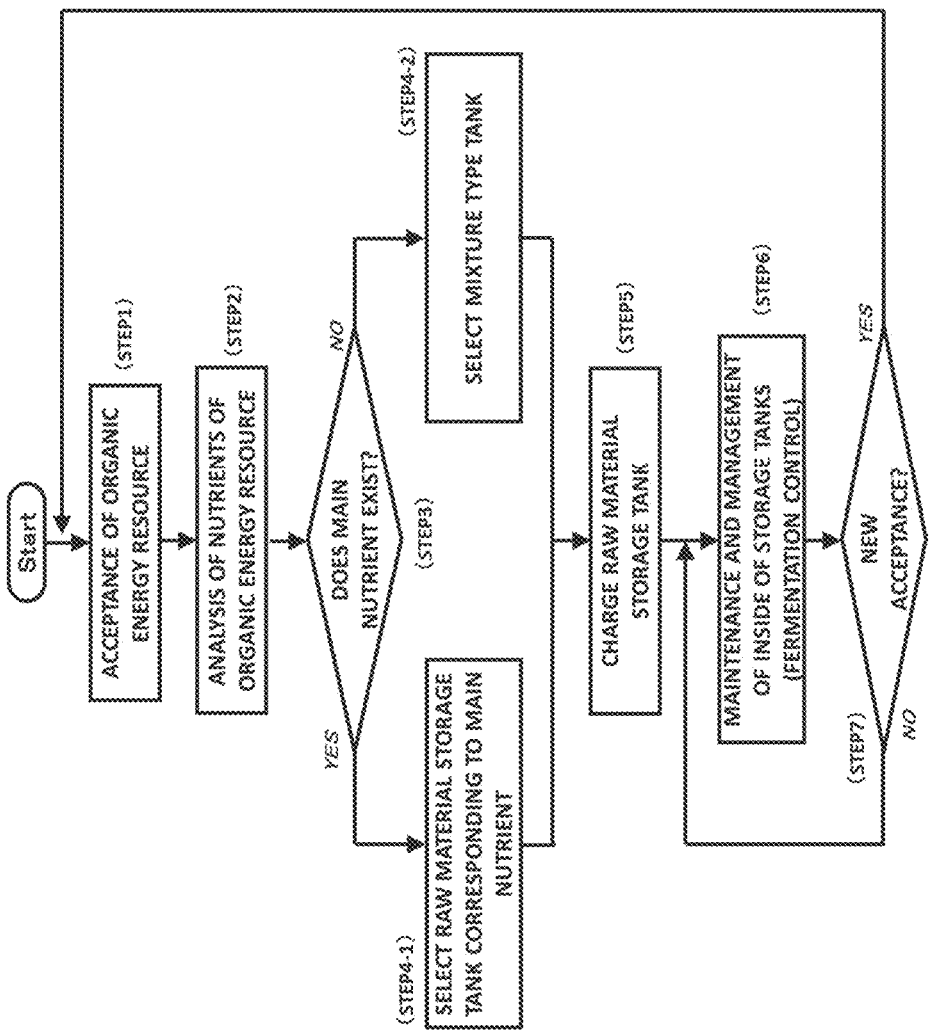
FIG. 1 is a flow chart depicting a biomass raw material storage method according to a first embodiment.

First, a biomass raw material storage method according to a first embodiment of the present invention is described suitably with reference to FIG. 1.

As depicted in FIG. 1, the biomass raw material storage method of the present embodiment is a method that can be used effectively, for example, in a biogas generation system that generates biogas from biomass raw material by anaerobic fermentation.

More particularly, the biomass raw material storage method of the present embodiment includes an acceptance step (step 1) of accepting an organic energy resource, a raw material analysis step (step 2) of analyzing the amount of nutrients contained in the accepted organic energy resource, a main nutrient specification step (step 3) of specifying a main nutrient of the organic energy resource on the basis of a result of the analysis, a raw material storage tank selection step (step 4) of selecting a raw material storage tank for storing the analyzed organic energy resource as biomass raw material from among a plurality of raw material storage tanks, in reference to the result of the analysis and according to the amounts of the nutrients contained in the organic energy resource, a charging step (step 5) of charging the selected raw material storage tank with the organic energy resource as biomass raw material, and a raw material fermentation controlling step (step 6) of controlling fermentation of the biomass raw material in the raw material storage tank in which the biomass raw material is stored.

It is to be noted that it is sufficient if the present invention includes the steps 2, 4, and 6, and in the following, specifically, the raw material analysis step, the raw material storage tank selection step, and the raw material fermentation controlling step are described in detail.

Raw Material Analysis Step

The raw material analysis step indicated by step 2 of FIG. 1 is a step of analyzing the amount of nutrients contained in the organic energy resource accepted in step 1.

The organic energy resource accepted in the acceptance step is provided to the raw material analysis step after undergoing a pulverization step as occasion demands.

It is to be noted that, in the biomass raw material storage method of the present embodiment, the organic energy resource is a resource that becomes what is generally called biomass raw material and includes food waste or organic waste other than food. The food waste includes, for example, processed food, seasoning, and so forth in addition to vegetables, fruits, fish, meat, and so forth. In the meantime, the organic waste includes wood, fallen leaves, flowers, and so forth.

As the nutrients that are contained in such organic energy resources as described above, carbohydrate, fat, protein, fiber, and so forth are available.

Conventionally, it has been pointed out that, in a biogas generation system, the generation efficiency of methane gas differs depending upon the nutrients of charged organic waste. This is because, for example, ammonia nitrogen is generated by decomposition of protein in food waste and inhibits methane fermentation or the like.

At the present point of time, the metabolism system of anaerobic fermentation has not been fully elucidated. Theoretically, the theoretical value of the methane gas generation amount of carbohydrate, fat and protein is pointed out to be 50%, 68%, and 71%, respectively (H. Schulz and B. Eder: Biogas-Praxis, Publishing Division of Ohmsha, Ltd., pp. 24 to 30 (2002)).

On the other hand, in actual methane fermentation, the fermentation performance depends upon such fermentation environments as the fermentation temperature, the concentration of ammonia nitrogen, pH, VFA (volatile fatty acid) concentration, and so forth.

In the present invention, as a result of earnest study by the inventors of the present invention, it has been found out that it is possible to control the fermentation of biomass raw material stored in a storage tank and store the biomass raw material safely for a long period of time, by analyzing nutrients of an organic energy resource and selecting an appropriate storage tank from among a plurality of storage tanks, according to the amounts of nutrients contained in the organic energy resource, and by maintaining and managing the plurality of storage tanks under individually different conditions.

Although, as the analysis method to be used in the raw material analysis step in the present embodiment, particularly, infrared spectroscopy by near-infrared rays or the like is applied preferably, this is not restrictive.

For example, in addition to infrared spectroscopy, any known analysis method capable of qualitatively and quantitatively analyzing nutrients in raw material can be used, and for example, fast liquid chromatography, a method by X-ray fluorescence elemental analysis, and so forth are applicable.

According to the raw material analysis step in the present embodiment, the type of nutrients and the content of the individual nutrients in an organic energy resource for which the analysis has been performed are clarified.

As the type of nutrients to be analyzed in the raw material analysis step, five types of "carbohydrate, fat, protein, fiber, and mixture type" are applied as described later. However, as long as the "mixture type" is essentially required, the classification is not restricted to that described above, and the types other than the "mixture type" can be set suitably.

Further, although the unit of the content of nutrients is preferably weight percent, this is not restrictive.

Further, according to a result of the analysis, a storage tank appropriate for storage of the organic energy source as biomass raw material is selected in the subsequent storage tank selection step 20.

Raw Material Storage Tank Selection Step

Now, the raw material storage tank selection step in the present embodiment is described.

The storage tank selection step indicated by step 4 of FIG. 1 is a step for selecting a raw material storage tank for storing an organic energy resource as biomass raw material, in reference to a result of the analysis in the raw material analysis step described above and according to the amount of nutrients contained in the organic energy resource. In particular, in the present embodiment, a plurality of raw material storage tanks T for storing biomass raw material are provided as described below.

In the present embodiment, the plurality of raw material storage tanks T preferably include a carbohydrate-rich tank T1, a fat-rich tank T2, a protein-rich tank T3, a fiber-rich tank T4, and a mixture type tank T5. Here, the carbohydrate-rich tank T1 is a tank for storing biomass raw material in which, among nutrients in a certain organic energy resource, carbohydrate is contained much as a main nutrient in comparison with other nutrients. Likewise, the fat-rich tank T2 is a tank for storing biomass raw material in which, among nutrients in a certain organic energy resource, fat is contained much as a main nutrient in comparison with other nutrients. Further, the protein-rich tank T3 is a tank for storing biomass raw material in which, among nutrients in a certain organic energy resource, protein is contained much as a main nutrient in comparison with other nutrients. Further, the fiber-rich tank T4 is a tank for storing biomass raw material in which, among nutrients in a certain organic energy resource, fiber is contained much as a main nutrient in comparison with other nutrients. Furthermore, the mixture type tank T5 is a tank for storing biomass raw material that contains, among nutrients in a certain organic energy resource, no nutrient that could be a main nutrient in comparison with the other nutrients.

It is to be noted that, in the present embodiment, the carbohydrate-rich tank T1 is set as a raw material storage tank for storing biomass raw material in which carbohydrate is contained by 50% or more. Likewise, the protein-rich tank T2 is set as a raw material storage tank for storing biomass raw material in which protein is contained by 50% or more; the fat-rich tank T3 is set as a raw material storage tank for storing biomass raw material in which fat is contained by 50% or more; the fiber-rich tank T4 is set as a raw material storage tank for storing biomass raw material in which fiber is contained by 50% or more; and the mixture type tank T5 is set as a raw material storage tank for storing biomass raw material in which no nutrient is contained by 50% or more as a main nutrient.

In particular, in the present embodiment, the mixture type tank T5 described above is installed as a storage tank for accommodating raw material that is not to be accommodated into any of the carbohydrate-rich tank T1, the fat-rich tank T2, the protein-rich tank T3, and the fiber-rich tank T4.

It is to be noted that, since, as hereinafter described in connection with a second embodiment, the mixture type tank T5 is a tank in which various nutrients are to be accommodated in a mixed manner, it may be set as a storage tank for preferentially accommodating raw material without any analysis of nutrients being performed.

In the storage tank selection step in the present embodiment, in which one of the carbohydrate-rich tank T1, the fat-rich tank T2, the protein-rich tank T3, and the fiber-rich tank T4 a certain organic energy resource that has undergone the raw material analysis step is to be accommodated is selected, and in a case where the organic energy resource is not to be accommodated in any one of the four tanks described above, it is accommodated in the mixture type tank T5.

It is to be noted that accepted raw material having undergone the raw material analysis step is in many cases accommodated in the mixture type tank T5.

It is to be noted that, although, in the present embodiment, the selection criteria in the storage tank selection step are set in such a manner as described above, the present invention is not restricted to such a setting as described above. For example, as the "raw material in which carbohydrate is contained much as a main nutrient," it is possible to set the carbohydrate-rich tank T1 as, for example, a storage tank for storing raw material in which "carbohydrate is contained by 40% or more and is contained most among the nutrients."

Anyway, in the storage tank selection step in the present embodiment, in a case where it is analyzed that a nutrient that is a main nutrient does not exist, the mixture type tank is selected, and for an organic energy resource that contains a nutrient that is a main nutrient, a raw material storage tank selected on the basis of the main nutrient is selected.

Further, although, in the present embodiment, the types of nutrients to be analyzed in the raw material analysis step are the four types of "carbohydrate, fat, protein, and fiber," they are not restricted to the four types and can be set suitably. For example, they may be set to the three types of "carbohydrate, fat, and protein." In this case, the plurality of raw material storage tanks T to be installed preferably include at least the three tanks of the "carbohydrate-rich tank, fat-rich tank, and protein-rich tank."

Raw Material Fermentation Controlling Step

Now, the raw material fermentation controlling step 30 in the present embodiment is described.

The raw material fermentation controlling step 30 indicated by step 6 of FIG. 1 is a step carried out in order to control methane fermentation of raw material in the raw material storage tank T selected in the storage tank selection step.

In particular, in the biogas generation system that generates biogas, supposed is such a situation that, before being subjected to the methane fermentation step, biomass raw material is stored for a long period of time or is transported. In this case, it is necessary to control fermentation of biomass raw material and generation of gas to appropriately maintain and manage the raw material in a storage tank T such that the raw material can be managed safely.

In particular, the biomass raw material in the storage tank T is maintained and managed through such parameters as the temperature, pH, liquid viscosity, alkalinity, VFA (volatile fatty acids and low fatty acids), and TS (total solids) (solid concentration).

Further, in the present embodiment, the carbohydrate-rich tank T1, the fat-rich tank T2, the protein-rich tank T3, the fiber-rich tank T4, and the mixture type tank T5 are preferably maintained and managed under conditions different from one another. It is to be noted that the raw material storage tanks may be maintained and managed under conditions different from one another as described above or may be maintained and managed under substantially same conditions as long as they are under control in fermentation.

In the following, an example of particular conditions in a case where the conditions for maintenance and management are different from one another as described above is described.

In the present embodiment, in the carbohydrate-rich tank T1, raw material in which carbohydrate is contained by 50% or more is accommodated. In a case where the three parameters of "temperature, pH, and liquid viscosity" are applied as the parameters for maintenance and management of the carbohydrate-rich tank T1, preferably they are individually maintained in the following ranges.

In particular, in the carbohydrate-rich tank T1, in order to control methane fermentation, it is preferable that the temperature be 30±5° C., pH be 3 to 6, and liquid viscosity be 0.5 to 20 Pa·s.

In this manner, in the present embodiment, preferably, the parameter for maintenance and management of a raw material storage tank in the raw material fermentation controlling step includes at least one of the temperature, pH, and liquid viscosity in the raw material storage tank, and at least one of the temperature, pH, and liquid viscosity differs among different raw material storage tanks.

It is to be noted that, in order to have each parameter for maintenance and management described above fall within a predetermined range, the inside of the raw material storage tank T may be heated or may have a known substance or the like added therein.

For example, in order to maintain the temperature in the carbohydrate-rich tank T1 within the range described above, a thermometer may be installed in the raw material storage tank such that the temperature is measured after every predetermined interval of time and heating or cooling is performed suitably by a known heating and cooling device.

Further, in order to maintain the pH in the carbohydrate-rich tank T1 within the range described hereinabove, the pH in the raw material storage tank may be measured after every predetermined interval of time and known acidic liquid (for example, organic acid such as formic acid or acetic acid) or alkaline liquid (for example, sodium hydroxide aqueous solution or the like) may be added.

It is to be noted that, although, in the present embodiment, the three parameters of "temperature, pH, and liquid viscosity" are applied as the parameter for maintenance and management of the inside of the carbohydrate-rich tank T1, the present invention is not limited to this, and it is also possible to use, for example, the two parameters of "temperature and pH."

The maintenance and management conditions for the fat-rich tank T2, the protein-rich tank T3, and the fiber-rich tank T4 can be set, for example, in the following manner.

(1) Fat-rich tank T2
temperature: 40±5° C.
pH: 3 to 6
liquid viscosity: 0.5 to 20 mPa·s
(2) Protein-rich tank T3
temperature: 30 to 70° C.
pH: 3 to 6
liquid viscosity: 1 to 15 mPa·s
(3) Fiber-rich tank T4
temperature: 20 to 50° C.
pH: 3 to 6
liquid viscosity: 5 to 20 mPa·s Now, the maintenance and management conditions for the mixture type tank T5 in the present embodiment are described.

In the present embodiment, in a case where the analyzed organic energy resource does not satisfy the accommodation conditions for the carbohydrate-rich tank T1, fat-rich tank T2, protein-rich tank T3 and fiber-rich tank T4, the analyzed organic energy resource is accommodated into the mixture type tank T5 as described hereinabove.

In particular, it can be predicted that the content of nutrients is biomass raw material accommodated in the mixture type tank T5 changes every time the mixture type tank T5 is charged with new raw material.

Therefore, in the present embodiment, it is possible to change the setting range for the parameters for maintenance and management of the mixture type tank T5 every time the mixture type tank T5 is charged with an organic energy resource as new biomass raw material.

For example, it is first supposed that biomass raw material N1 is accommodated by 100 Kg in the mixture type tank T5. It is assumed that, in regard to the content of nutrients of the biomass raw material N1, carbohydrate amounts to 40 weight percent, fat amounts to 30 weight percent, protein amounts to 15 weight percent, and fiber amounts to 15 weight percent.

At this point of time, the range of the parameters for the mixture type tank T5 is set in the following manner:
temperature: 20 to 35° C.
pH: 3 to 6
liquid viscosity: 10 to 20 mPa·s Then, it is supposed that biomass raw material N2 is newly added by 100 Kg into the mixture type tank T5. It is assumed that, in regard to the content of nutrients of the biomass raw material N2, carbohydrate amounts to 40 weight percent, fat amounts to 40 weight percent, protein amounts to 20 weight percent, and fiber amounts to 0 weight percent.

Consequently, at the point of time when the biomass raw material N2 is newly added into the mixture type tank T5, in regard to the content of nutrients in the mixture type tank T5, carbohydrate amounts to 40 weight percent, fat amounts to 35 weight percent, protein amounts to 17.5 weight percent, and fiber amounts to 7.5 weight percent.

In a case where the mixture type tank T5 is charged afresh with the biomass raw material N2, it is possible to change the range for the parameters for maintenance and management in the following manner.
temperature: 20 to 40° C.
pH: 3 to 6
liquid viscosity: 10 to 20 mPa·s It is to be noted that, although, in the example described above, only the condition for the temperature is changed, the condition may be changed for at least one of the temperature, pH, and liquid viscosity.

By changing the setting range for the parameters for maintenance and management of the mixture type tank T5 in this manner, it is possible to appropriately control the fermentation of biomass raw material accommodated in the mixture type tank T5.

It is to be noted that the timing of such a change of the setting range may be the point of time when the raw material storage tank T is charged with new raw material, or the setting range may be set to an appropriate range by periodically detecting nutrients in the tank and selecting the appropriate range at that point of time.

Further, the upper limit and the lower limit of the setting range can be set appropriately taking the type of nutrients in the raw material, ambient temperature, or the like into consideration.

It is to be noted that, in order to have the parameters for maintenance and management of the fat-rich tank T2, the protein-rich tank T3, the fiber-rich tank T4, and the mixture type tank T5 fall within respective predetermined ranges, the inside of them may be heated or a known substance or the like may be added as in the description made with respect to the carbohydrate-rich tank T1.

Biomass Raw Material Storage System

Now, a biomass raw material storage system 200 according to the present embodiment is described with reference to FIG. 2.

Figure 2:
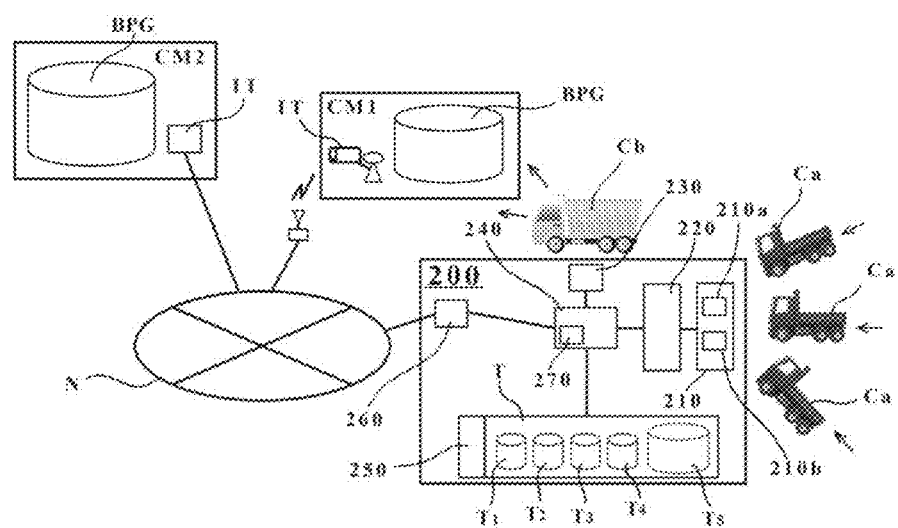
FIG. 2 is a schematic view of a biomass raw material storage system.
Figure 3:
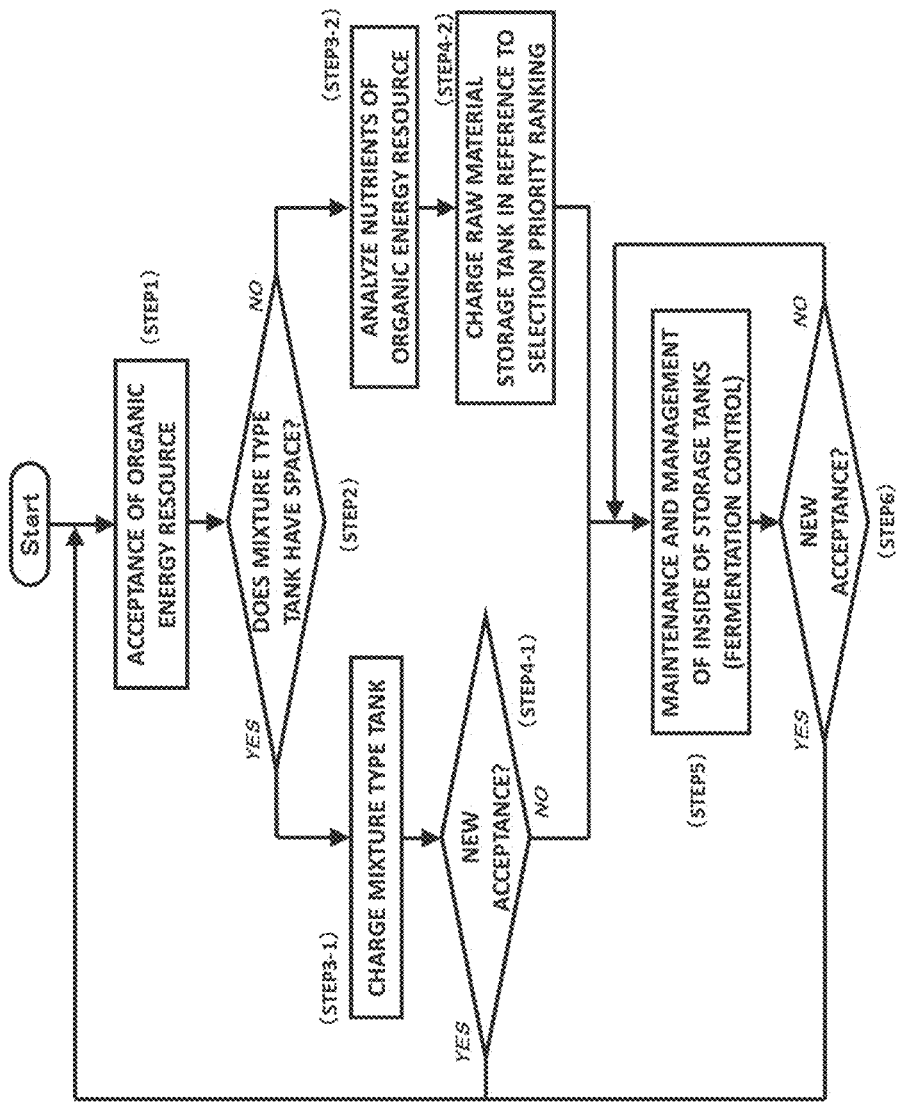
FIG. 3 is a flow chart depicting a biomass raw material storage method according to a second embodiment.

As depicted in FIG. 2, the biomass raw material storage system 200 can communicate with biomass power generation business operators CM1 and CM2, which have biomass power generation equipment BPG, through a known network N such as the Internet. It is to be noted that, although it is exemplified in FIG. 2 that a total of two business operators are individually equipped with an information terminal IT such as a PC (personal computer) or a smartphone, the business operators connected to the biomass raw material storage system 200 through the network N and locations of them are not limited to any specific kind, and a countless number of such business operators can be present in a local area or all over the country.

More particularly, the biomass raw material storage system 200 of the present embodiment includes resource acceptance means 210 for accepting an organic energy resource, nutrient analysis means 220 for analyzing nutrients of the organic energy resource accepted by the resource acceptance means 210, main nutrient specification means 230 for specifying a main nutrient that is the main nutrient from among the analyzed nutrients, a plurality of raw material storage tanks T for storing the organic energy resource as biomass raw material, raw material storage tank selection means 240 for selecting a storage destination from among the plurality of different raw material storage tanks T classified for individual main nutrients in reference to the specified main nutrient, and raw material fermentation controlling means 250 for controlling fermentation of the biomass raw material in the storage tank in which the biomass raw material is stored.

It is to be noted that, in the present embodiment, preferably, the biomass raw material storage system 200 further includes reception means 260 for receiving information regarding biomass raw material to be used by a client (biomass power generation. business operators CM1 or CM2) and supply biomass raw material determination means 270 for determining a storage tank for the biomass raw material to be supplied to the client, in reference to components of the biomass raw material of the client. As a particular example of the reception means 260 and the supply biomass raw material determination means 270, a known computer that functions also as the main nutrient specification means 230 and the raw material storage tank selection means 240 described later can be exemplified.

Consequently, for example, in a case where biomass raw material containing much carbohydrate is required by the biomass power generation equipment BPG of the biomass power generation business operator CM1, it is possible to supply biomass raw material containing much carbohydrate from the carbohydrate-rich tank T1 to the biomass power generation business operator CM1 through a supply vehicle Cb in response to the needs for the biomass raw material.

Here, as depicted in FIG. 2, the resource acceptance means 210 may include neutralization mixture fluidization means 210a that fluidizes the organic energy resource including liquid or sludge and crushing means 210b that includes a crusher for crushing the organic energy resource other than the liquid or the sludge described hereinabove.

As the neutralization mixture fluidization means 210a, a known vessel with a mixer which stores, neutralizes, and mixes, among the accepted organic energy resource, for example, liquid substance (substance containing water, carbohydrate, fat, protein, and fiber in a mixed state), sludge, and so forth can be exemplified.

The crushing means 210b is a vessel equipped with a known roller mill or jet mill and stores an organic energy resource that is high in particle size in comparison with such liquid and sludge as described above.

In this manner, in the biomass raw material storage system 200 of the present embodiment, a different destination tank for acceptance is selected depending upon the state (size, density, and so forth of grain) of an organic energy resource at the time of acceptance. Further, as depicted in FIG. 2, a transport vehicle Ca on which various organic energy resources are loaded can carry an organic energy resource into the resource acceptance means 210.

The plurality of raw material storage tanks T include, in the present embodiment, the carbohydrate-rich tank T1, the fat-rich tank T2, the protein-rich tank T3, the fiber-rich tank T4, and the mixture type tank T5. As described hereinabove, such classification of them as described above is an example, and, for example, one of them other than the mixture type tank T5 may be omitted.

Further, as apparent from the illustration, the mixture type tank T5 has a capacity greater than those of the other raw material storage tanks. Furthermore, for each raw material storage tank T, an unillustrated sensor is provided such that the amount of biomass raw material stored in the storage tank can be detected.

To the nutrient analysis means 220, known infrared spectroscopy by near-infrared rays or the like is applied preferably as described hereinabove. Further, in addition to infrared spectroscopy, any known analysis method capable of qualitatively and quantitatively analyzing nutrients in an organic energy resource can be used.

Although, as an example, the near-infrared analyzer NIR-Master manufactured by Nihon BUCHI K. K. is used in the present embodiment, this is not restrictive.

The main nutrient specification means 230 is a known computer including a CPU (central processing unit) and a memory. The main nutrient specification means 230 performs the analysis described hereinabove in connection with the raw material analysis step, in reference to a result of the analysis by the nutrient analysis means 220. Consequently, since types and amounts of nutrients contained in the analyzed organic energy resource are specified, which one of the nutrients is a main nutrient is specified.

The raw material storage tank selection means 240 has a function of selecting a storage destination in reference to selection priority ranking determined in advance. The raw material storage tank selection means 240 is a known computer that includes a CPU and a memory and functions also as the main nutrient specification means 230.

It is to be noted that the selection priority ranking described above may be stored as electronic data in the memory.

The substance of the selection. priority ranking in the present embodiment is (α) that, when it is analyzed that a nutrient that is a main nutrient does not exist, the mixture type tank T5 is selected and (β) that, for an organic energy resource that contains a nutrient that is a main nutrient, a raw material storage tank classified for the main nutrient is selected.

It is to be noted that the selection priority ranking described above is an example, and alternatively, the mixture type tank T5 may be determined as a selection destination of the highest priority whereas, for an organic energy resource that contains a nutrient that is a main nutrient, a raw material storage tank classified for the main nutrient is selected next, for example, as in a second embodiment hereinafter described.

The raw material fermentation controlling means 250 has a function of controlling the fermentation of biomass raw material stored in each raw material storage tank T, by the method described hereinabove in connection with the raw material fermentation controlling step. More particularly, in each raw material storage tank T, various measuring instruments such as a thermometer, a pH meter, a liquid viscometer, an alkaline meter, and a VFA meter that are not illustrated are arranged, and parameters measured by the instruments are maintained and managed by the raw material fermentation controlling means 250 such that they fall within. the predetermined ranges.

Industrial Applicability

As described above, according to the biomass raw material storage method and the biomass raw material storage system of the present invention, biomass raw material can be stored safely for a predetermined period of time while the fermentation of the biomass raw material is controlled, and this can contribute to raw material supply to many pieces of biomass generation equipment.

It is to be noted that, although the embodiment has been described focusing on control of the fermentation of raw material, it is also possible to apply the present invention to efficient methane fermentation and high-efficient methane gas generation.

Reference Signs List

200: Biomass raw material storage system
210: Resource acceptance means
220: Nutrient analysis means
230: Main nutrient specification means
240: Raw material storage tank selection means
250: Raw material fermentation controlling means
260: Reception means
270: Supply biomass raw material determination means
BPG: Biomass power generation equipment
CM: Biomass power generation business operator

The invention claimed is:

1. A biomass raw material storage method comprising:
a raw material analysis step of analyzing an amount of nutrients contained in an accepted organic energy resource;
a raw material storage tank selection step of selecting, from among a plurality of raw material storage tanks, a raw material storage tank for storing the analyzed organic energy resource as biomass raw material, in reference to a result of the analysis and according to the amount of nutrients contained in the accepted organic energy resource; and
a raw material fermentation controlling step of controlling fermentation of the biomass raw material in the raw material storage tank in which the biomass raw material is stored,
wherein the plurality of raw material storage tanks include at least a carbohydrate-rich tank, a fat-rich tank, a protein-rich tank, a fiber-rich tank, and a mixture tank, and the tanks are maintained and managed under conditions different from one another.

2. The biomass raw material storage method according to claim 1, wherein,
in the storage tank selection step,
the mixture tank is selected when it is analyzed that a specified nutrient does not exist among the nutrients, and,
for the organic energy resource that contains a nutrient that is the specified nutrient, the raw material storage tank classified for the nutrient that is the specified nutrient is selected.

3. The biomass raw material storage method according to claim 1, wherein,
in the storage tank selection step,
the mixture tank is a selection destination of the highest priority, and,
for the organic energy resource that contains a nutrient that is the specified nutrient, the raw material storage tank classified for the nutrient that is the specified nutrient is selected next.

4. The biomass raw material storage method according to claim 1, wherein
a parameter for maintenance and management of a raw material storage tank in the raw material fermentation controlling step includes at least one of a temperature and a pH in the raw material storage tank, and
the temperature or the pH is managed in such a manner as to be different among different ones of the raw material storage tanks.

5. A biomass raw material storage system comprising:
resource acceptance means for accepting an organic energy resource;
nutrient analysis means for analyzing nutrients of the organic energy resource accepted by the resource acceptance means;
nutrient specification means for specifying a main nutrient that is a specified nutrient among the analyzed nutrients;
a plurality of raw material storage tanks each for storing the organic energy resource as biomass raw material;
raw material storage tank selection means for selecting a storage destination from among the plurality of raw material storage tanks that are different from one another and are classified for the individual nutrients, in reference to the specified nutrient, wherein the plurality of raw material storage tanks include at least a carbohydrate-rich tank, a fat-rich tank, a protein-rich tank, a fiber-rich tank, and a mixture tank, and the tanks are maintained and managed under conditions different from one another; and
raw material fermentation controlling means for controlling fermentation of the biomass raw material in a storage tank in which the biomass raw material is stored.

6. The biomass raw material storage system according to claim 5, wherein
the resource acceptance means includes
neutralization mixture fluidization means for fluidizing the organic energy resource including liquid or sludge, and
crushing means including a crusher for crushing the organic energy resource other than the liquid or the sludge.

7. The biomass raw material storage system according to claim 5, wherein the raw material storage tank selection means selects the storage destination in reference to selection priority ranking determined in advance, and the selection priority ranking is made such that the mixture tank is a selection destination of the highest priority and a storage destination corresponding to the analyzed specified nutrient is selected next.

8. The biomass raw material storage system according to claim 5, further comprising:
reception means for receiving information regarding biomass raw material used by a client; and
supply biomass raw material determination means for determining a storage tank for the biomass raw material to be supplied to the client, in reference to nutrients of the biomass raw material of the client.

* * * * *